(12) United States Patent
Reid et al.

(10) Patent No.: US 7,683,231 B2
(45) Date of Patent: Mar. 23, 2010

(54) CATALYST AND PROCESS FOR THE PRODUCTION OF OLEFINS

(75) Inventors: Ian Allan Beattie Reid, London (GB); Vaughan Clifford Williams, Staines (GB)

(73) Assignee: Ineos Europe Limited, Hampshire (GB)

( * ) Notice: Subject to any disclaimer, the term of this patent is extended or adjusted under 35 U.S.C. 154(b) by 612 days.

(21) Appl. No.: 10/558,827

(22) PCT Filed: May 18, 2004

(86) PCT No.: PCT/GB2004/002132

§ 371 (c)(1),
(2), (4) Date: Nov. 29, 2005

(87) PCT Pub. No.: WO2004/108279

PCT Pub. Date: Dec. 16, 2004

(65) Prior Publication Data

US 2007/0043252 A1  Feb. 22, 2007

(30) Foreign Application Priority Data

Jun. 5, 2003 (GB) ................................. 0312966.5

(51) Int. Cl.
*C07C 4/06* (2006.01)
*B01J 23/00* (2006.01)

(52) U.S. Cl. .............. 585/652; 585/651; 585/653; 502/325; 502/439; 502/527.16; 502/527.19; 502/527.24

(58) Field of Classification Search ......... 585/651–653, 585/658; 502/439, 527.16, 527.19, 527.2, 502/527.24
See application file for complete search history.

(56) References Cited

U.S. PATENT DOCUMENTS 4,154,568 A * 5/1979 Kendall et al. ................. 431/7
4,836,988 A * 6/1989 Kristof et al. ............... 422/171
5,382,741 A    1/1995 Astbury et al.
5,552,360 A * 9/1996 Farrauto et al. ............. 502/178
5,905,180 A    5/1999 Yokoyama et al.
5,937,641 A    8/1999 Graham et al.
6,203,771 B1 * 3/2001 Lester et al. ................. 423/219
6,254,807 B1   7/2001 Schmidt et al.
6,365,543 B1   4/2002 Schmidt et al.
6,395,944 B1   5/2002 Griffiths et al.
6,433,234 B1 * 8/2002 Griffiths et al. ............. 585/324
7,074,977 B2 * 7/2006 Rapier et al. ................ 585/324

FOREIGN PATENT DOCUMENTS

| EP | 0 332 289 | 9/1989 |
| EP | 0 931 590 A1 | 7/1999 |
| WO | WO 97/26987 A1 | 7/1997 |
| WO | WO 00/14036 A1 | 3/2000 |
| WO | WO 00/14180 | 3/2000 |
| WO | WO 00/28196 | 5/2000 |
| WO | WO 01/68571 A1 | 9/2001 |
| WO | WO 02/04388 A1 | 1/2002 |
| WO | WO 02/04389 * | 1/2002 |

OTHER PUBLICATIONS

Yokoyama, C., et al; "Platinum-tin and platinum-copper catalysts for autothermal oxidative dehydrogenation of ethane to ethylene"; *Catalysts Letters*; vol. 38, pp. 181-188 (1996).

* cited by examiner

*Primary Examiner*—In Suk Bullock
(74) *Attorney, Agent, or Firm*—Nixon & Vanderhye

(57) ABSTRACT

A catalyst system capable of supporting combustion beyond the fuel rich limit of flammability comprising a catalytic component, a first support and a second support and wherein the catalytic component is present on both the first and the second support, and a process for the production of an olefin, said process comprising passing a mixture of a hydrocarbon and an oxygen-containing gas over said catalyst system to produce said olefin. The first support and the second support must differ in at least one of the following aspects: support material, support type and/or structural dimension.

16 Claims, No Drawings

CATALYST AND PROCESS FOR THE PRODUCTION OF OLEFINS

This application is the U.S. National Phase of International Application PCT/GB04/002132, filed 18 May 2004, which designated the U.S. PCT/GB04/002132 claims priority to British Application No. 0312966.5 filed 5 Jun. 2003. The entire content of these applications are incorporated herein by reference.

The present invention relates to a process for the production of olefins from hydrocarbons in which the hydrocarbons are treated to autothermal cracking.

Autothermal cracking is a route to olefins in which the hydrocarbon feed is mixed with oxygen and passed over an autothermal cracking catalyst. The autothermal cracking catalyst is capable of supporting combustion beyond the fuel rich limit of flammability. Combustion is initiated on the catalyst surface and the heat required to raise the reactants to the process temperature and to carry out the endothermic cracking process is generated in situ. Generally the hydrocarbon feed and the oxygen is passed over a single catalyst bed to produce the olefin product. Typically, the catalyst bed comprises at least one platinum group metal, for example, platinum, supported on a catalyst support. The autothermal cracking process is described in EP 332289B; EP-529793B; EP-A-0709446 and WO 00/14035.

The catalyst supports are usually ceramic materials and are usually in the form of foams, pellets, beads, spheres, monoliths, tablets and/or extrudates. The properties of each type of support vary and each support may possess properties that are both advantageous and problematic when they are used as a support for an autothermal cracking catalyst.

Many supports tend not to be chemically inert in the autothermal cracking reaction and consequently the support tends to degrade. Other supports may be thermally unstable or unstable to thermal shock, which results in support cracking. Some supports may be structured to provide various flow regimes for the gaseous reactants. Highly tortuous materials provide good mixing of the reactants and promote reaction stability but create a high pressure drop in the autothermal reactor due to turbulent gas flow which leads to excessive force being applied to the catalyst which can lead to structural collapse. Other supports that provide a laminar flow lead to a low pressure drop but tend not to be able maintain the reaction stability effectively.

Finally some supports exhibit a differential expansion rate to that of the catalyst holder. The catalyst is usually positioned in a metallic holder in the autothermal reactor. During the autothermal cracking reaction both the holder and the catalyst expand as a result of the heat generated from the reaction. Initially the catalyst increases in temperature and expands as the reaction occurs on the surface of the catalyst. However at this stage the expansion of the holder is not as pronounced as that of the catalyst because the heat generated from the reaction hasn't had the opportunity to pass to the holder. Consequently the catalyst is crushed against the walls of the holder. As the reaction continues the holder expands to a greater extent than the catalyst. As a result a space develops between the holder and the catalyst and the reactants bypass the catalyst.

Consequently there is a need to provide supports that exhibit an improved performance in the autothermal reactor and which can be tailored to provide different functionality through the catalyst bed.

It has now been found that the autothermal cracking process can be improved by employing a catalyst system comprising at least two different support materials.

Accordingly, the present invention provides a catalyst system capable of supporting combustion beyond the fuel rich limit of flammability comprising a catalytic component, a first support and a second support and wherein the catalytic component is present on both the first and the second support.

The catalyst system may further comprise at least one further support e.g. a third support and optionally a fourth.

The present invention also provides a process for the production of an olefin, said process comprising passing a mixture of a hydrocarbon and an oxygen-containing gas over a catalyst system as herein described above to produce said olefin.

Preferably, the catalyst component comprises a Group VIIIB metal. Suitable Group VIIIB metals include platinum, palladium, ruthenium, rhodium, osmium and iridium. Preferably, the Group VIIIB metal is selected from rhodium, platinum, palladium or mixtures thereof. Especially preferred are platinum, palladium or mixtures thereof. Typical Group VIIIB metal loadings range from 0.01 to 50 wt %, preferably, from 0.01 to 20 wt %, and more preferably, from 0.01 to 10 wt %, for example 1-5 wt %, such as 3-5 wt %. Suitably, the first catalyst bed comprises platinum or palladium, especially platinum.

Preferably the catalyst component may be a promoted catalyst component such as a promoted Group VIIIB metal catalyst. The promoter may be selected from the elements of Groups IIIA, IVA and VA of the Periodic Table and mixtures thereof. Alternatively, the promoter may be a transition metal; the transition metal being a different metal to the catalyst component, such as the Group VIIIB metal(s) employed as the catalytic component.

The promoter may also be selected from any of the lanthanide metal oxides.

Preferred Group IIIA metals include Al, Ga, In and Tl. Of these, Ga and In are preferred. Preferred Group IVA metals include Ge, Sn and Pb. Of these, Ge and Sn are preferred, especially Sn. The preferred Group VA metal is Sb. The atomic ratio of Group VIIIB metal to the Group IIIA, IVA or VA metal may be 1:0.1-50.0, preferably, 1:0.1-12.0, such as 1:0.3-5.

Suitable transition metal promoters may be selected from any one or more of Groups IB to VIIIB of the Periodic Table. In particular, transition metals selected from Groups IB, IIB, VIB, VIIB and VIIIB of the Periodic Table are preferred. Examples of such transition metal promoters include V, Ni, Ta, Cr, Mo, W, Mn, Re, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn, especially Cu. The atomic ratio of the Group VIIIB metal to the transition metal promoter may be 1:0.1-50.0, preferably, 1:0.1-12.0.

Specific examples of promoted Group VIIIB metals for use as the promoted catalyst component include Pt/Ga, Pt/In, Pt/Sn, Pt/Ge, Pt/Cu, Pd/Sn, Pd/Ge, Pd/Cu and Rh/Sn. Where the Group VIIIB metal is Rh, Pt or Pd, the Rh, Pt or Pd may comprise between 0.01 and 5.0 wt %, preferably, between 0.01 and 3.0 wt %, and more preferably, between 0.5 and 3.0 wt % of the total weight of the catalyst. The atomic ratio of Rh, Pt or Pd to the Group IIIA, IVA, VA or transition metal promoter may be 1:0.1-50.0, preferably, 1:0.1-12.0. For example, atomic ratios of Rh, Pt or Pd to Sn may be 1:0.1 to 50, preferably, 1:0.1-12.0, more preferably, 1:0.2-5.0 and most preferably, 1:0.3-5.0. Atomic ratios of Pt or Pd to Ge may be 1:0.1 to 50, preferably, 1:0.1-12.0, and more preferably, 1:0.5-8.0. Atomic ratios of Pt or Pd to Cu may be 1:0.1-3.0, preferably, 1:0.2-2.0, and more preferably, 1:0.5-1.5.

For the avoidance of doubt, the catalyst component and the promoter may be present in any form, for example, as a metal, or in the form of a metal compound, such as an oxide.

The first and second support may be selected from a range of support materials.

The support material may be a ceramic or metallic material. Wherein the support material is ceramic the support may be any oxide, nitride carbide or combination thereof that is stable at high temperatures of, for example, between 600° C. and 1200° C. The ceramic support material preferably has a low thermal expansion co-efficient, is chemically inert and is resistant to phase separation at high temperatures.

Suitable ceramic supports include alumina, silica-alumina, a combination of alumina and mullite, lithium aluminium silicate, cordierite, silicon carbide, zirconia toughened alumina, partially stabilized zirconia, fully stabilized zirconia, spinel, chromia, titania, aluminium titanate, or any combination of the above. Wherein the support is either fully or partially stabilized, the stabilizers used are usually selected from magnesium oxide, yttrium oxide and calcium oxide.

The support material may also be selected from a metal. Suitable metals may include steel (mild and high carbon), stainless steel, Hastaloy, Ni-Chrome, Inconel, Monel, nickel, copper, iron, platinum, noble metals and their alloys, cobalt, FeCrAlY, NiCrAlY, or any alloy containing Y, Cr, Fe, Ni and Al e.g. Kanthal, Incoloy MA956 or CoCrAlY. Small amounts of other elements, such as Si, Ti, Nb, Mo, W, Zr, Mg and Cu, may also be present.

Preferably the metal has a melting point of greater than 1200° C., and most preferably, the metal is selected from FeCrAlY, NiCrAlY, CoCrAlY, Ni-Chrome, and any grade of Inconel and Monel.

Preferably, both the first and second support materials are ceramic materials.

The support type could be selected from anyone of the following; foams, channeled monoliths, mats, fibres, gauzes, pellets, beads, spheres, tablets and/or extrudates.

The structural dimensions of the support type may also vary.

Wherein the support is in the form of a foam, the foams usually have a pore size in the range of 10 ppi to 100 ppi and preferably between 30 to 45 ppi. These foams typically have a density of from between 60% to 99% of theoretical density of a fully dense material.

Wherein the support material is in the form of a monolith the monolith is provided with channels. These channels may be of any suitable shape the preferred ones being square, rectangular, triangular, hexagonal and circular. Typically the channels do not pass directly through the monolith and usually the channels provide a complex passageway through the monolith. Usually the monolith has between 2000 cpi (cells per inch) to 5 cpi and preferably between 1000 cpi to 10 cpi.

Wherein the support is in the form of a gauze the wire thickness is usually from 0.1 mm to 3 mm with a mesh size of from 250 wires per inch to 4 wires per inch.

Wherein the support is in the form of pellets, beads, spheres, tablets and/or extrudates the external dimensions are usually within the range of between 0.1 mm-50 mm and advantageously within the range of 0.5 mm to 20 mm.

The catalyst system employed in the present invention may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support may then be reduced, for example, by heat treatment in a hydrogen atmosphere.

Prior to the addition of the catalyst component to the supports a refractory metal oxide coating may be deposited upon the first and/or second support. The refractory metal oxide coating may comprise at least one Group II, III or IV metal oxide. Preferably the support coatings comprise at least one of the refractory metal oxides selected from alumina, zirconia, baria-alumina or magnesia. The most preferred support coating is alumina, and advantageously the alumina is stabilized with a rare earth metal oxide and or alkaline earth metal oxide.

For the avoidance of doubt it is a feature of the present invention that the first support and the second support must differ in at least one of the following aspects; support material, support type and/or structural dimension.

Consequently the first support may be formed from the same material (e.g. alumina) and be of the same support type (e.g. foam) as the second support on the condition that the supports have different structural dimensions (e.g. pore size).

In this embodiment of the invention the catalyst system may comprise a support structure formed from the same material and of the same support type but exhibit a gradual change in pore size throughout the support structure. In this embodiment at least one first region of the support structure will constitute a first support and at least one second region of the support structure will constitute a second support by virtue of their differing structural dimensions.

Similarly the first support may be formed from the same material (e.g. alumina) and have the same structural dimensions (e.g. pore size) on the condition that the supports are of different support types i.e. the first support may be an extrudate and the second support may be a foam.

Finally the first support may be of the same support type i.e. a foam with the same structural dimensions (i.e. pore size) as the second support on the condition that the supports are formed from different materials i.e. the first support may be formed from a metal and the second support may be formed from a ceramic, such as alumina.

Preferably the first and second supports may differ in more than one aspect i.e. different support material and/or different support type and/or different structural dimensions.

The first and second supports may occupy various positions in the reactor. Usually one support is located upstream of the other with respect to the directional flow of the reactants. Alternatively one support may be positioned such that it occupies at least a part of the external surface area of the catalyst system with the other support occupying the internal surface area of the catalyst system.

Wherein the first or second support is in the form of a foam, monolith or gauze the support preferably comprises a series of blocks or layers that tessellate together to leave no gaps. Preferably these blocks or layers are tiled within the reactor in different directions and most preferably in a manner such that tiles of a layer either above or below do not exactly overlap with any neighbouring layer.

Preferably, the first support is located in the reactor upstream of the second support with respect to the directional flow of the reactants, and the first support provides a higher pressure drop per unit length (in the direction of flow of the reactants) than the second support.

In a preferred embodiment of the invention the first support is a foam and the second support is a monolith wherein the first support is located in the reactor upstream of the second support with respect to the directional flow of the reactants. In this particular embodiment of the invention the foam initially creates reaction stability wherein the reactants are thoroughly mixed within the porous structure of the foam and then the reaction continues throughout the monolith which provides a lower overall pressure drop through the reactor.

A similar advantageous result may be achieved where the first support is a porous foam comprising small pores and the second support is also a foam comprising larger pores wherein the first support is located in the reactor upstream of the second support with respect to the directional flow of the reactants.

In another embodiment of the invention the first support may be located in the reactor upstream of the second support with respect to the directional flow of the reactants and down the sides of the second support. In this particular embodiment the first support may be in the form of beads and the second support may be in the form of a foam or a monolith. Wherein the catalyst holder and the second support create a circumferential gap due to differential expansion during the reaction the first support may move to fill the space between the second support and the catalyst holder. Consequently this prevents the bypassing of the reactant gases around the second support. In this way the catalyst system becomes self sealing with the holder.

Where the first support is located upstream of the second support with respect to the directional flow of the reactants, including where the first support is also located down the sides of the second support, there may be at least one further support downstream of the second support (with respect to the directional flow of the reactants). The further support or supports may have present thereon the same catalytic component as is present on the first and second supports or may have present thereon a catalytic component ("further catalytic component") which is different to the catalytic component on the first and second supports. In addition, said further support or supports may be the same or different to either of the first or second catalyst supports, or to any other further catalyst supports which are present.

Preferably, there is present a first support, a second support and a third support, wherein the first support is located in the reactor upstream of the second support with respect to the directional flow of the reactants and the second support is located in the reactor upstream of the third support with respect to the directional flow of the reactants, and wherein and the first support and third support both provide a higher pressure drop per unit length (in the direction of flow of the reactants) than the second support. Most preferably the third support comprises a catalytic component which catalyses the consumption of any unreacted oxygen, typically by reaction with hydrogen and/or carbon monoxide in the product stream. Suitable catalytic components include promoted Group VIIIB metal catalysts, as previously described.

It is usually advantageous to provide a first support located in the reactor upstream of the second support wherein the first support is more thermally resistant than the second support.

Advantageously the first support may be a ceramic support and the second support may be a metallic support wherein the first support is located in the reactor upstream of the second support with respect to the directional flow of the reactants. This provides a support which is stronger by virtue of the metallic second support but is capable of withstanding excessive front face temperatures by virtue of the ceramic second support.

Similarly the first support may be a cordierite support and the second support may be an alumina support wherein the first support is located in the reactor upstream of the second support with respect to the directional flow of the reactants. The cordierite support prevents damage to the alumina support from thermal shock and the alumina provides a support material that is more chemically inert.

It is also a feature of the present invention that the same catalyst component or wherein a promoted catalyst component is employed the same promoted catalyst component must be present on each of the first and second support. However it should be noted that the percentage loadings of the catalyst component or the promoted catalyst component may differ on each of the first and second support. Preferably the percentage loadings of the catalyst component or the promoted catalyst component on each of the first and second support are the same. Advantageously the catalyst component or the same promoted catalyst component are distributed substantially uniformly throughout the support.

Preferably a non catalytic resistance zone is located upstream of the catalyst system. The resistance zone usually comprises a network of capillaries or channels and most preferably the resistance zone comprises a porous material and advantageously the porous material is a non metal e.g. a ceramic material. Suitable ceramic materials include lithium aluminium silicate (LAS), alumina ($\alpha$-$Al_2O_3$), yttria-stabilised zirconia and alumina titanate. A preferred porous material is gamma alumina. The porous material may be in the form of spheres, other granular shapes or ceramic foams. Typically the resistance zone has between 10-60 pores per square inch, preferably between 20-50 pores per square inch and most preferably between 30-45 pores per square inch.

The process of the present invention may be used to convert both liquid and gaseous hydrocarbons into olefins. Suitable liquid hydrocarbons include naphtha, gas oils, vacuum gas oils and mixtures thereof. Preferably, however, gaseous hydrocarbons such as ethane, propane, butane and mixtures thereof are employed. Suitably, the hydrocarbon is a paraffin-containing feed comprising hydrocarbons having at least two carbon atoms.

The hydrocarbon feed is mixed with any suitable oxygen-containing gas. Suitably, the oxygen-containing gas is molecular oxygen, air, and/or mixtures thereof. The oxygen-containing gas may be mixed with an inert gas such as nitrogen or argon.

Additional feed components may be included, if so desired. Suitably, hydrogen, carbon monoxide, carbon dioxide or steam may be co-fed into the reactant stream.

Any molar ratio of hydrocarbon to oxygen-containing gas is suitable provided the desired olefin is produced in the process of the present invention. The preferred stoichiometric ratio of hydrocarbon to oxygen-containing gas is 5 to 16, preferably, 5 to 13.5 times, preferably, 6 to 10 times the stoichiometric ratio of hydrocarbon to oxygen-containing gas required for complete combustion of the hydrocarbon to carbon dioxide and water.

The hydrocarbon is passed over the catalyst system at a gas hourly space velocity of greater than 10,000 $h^{-1}$, preferably above 20,000 $h^{-1}$ and most preferably, greater than 100,000 $h^{-1}$. It will be understood, however, that the optimum gas hourly space velocity will depend upon the pressure and nature of the feed composition.

Preferably, hydrogen is co-fed with the hydrocarbon and oxygen-containing gas into the reaction zone. The molar ratio of hydrogen to oxygen-containing gas can vary over any operable range provided that the desired olefin product is produced. Suitably, the molar ratio of hydrogen to oxygen-containing gas is in the range 0.2 to 4, preferably, in the range 1 to 3.

Hydrogen co-feeds are advantageous because, in the presence of the catalyst system, the hydrogen combusts preferentially relative to the hydrocarbon, thereby increasing the olefin selectivity of the overall process.

Preferably, the reactant mixture of hydrocarbon and oxygen-containing gas (and optionally hydrogen co-feed) is preheated prior to contact with the catalyst. Generally, the reactant mixture is preheated to temperatures below the autoignition temperature of the reactant mixture.

Advantageously, a heat exchanger may be employed to preheat the reactant mixture prior to contact with the catalyst system. The use of a heat exchanger may allow the reactant mixture to be heated to high preheat temperatures such as temperatures at or above the autoignition temperature of the reactant mixture. The use of high pre-heat temperatures is beneficial in that less oxygen reactant is required which leads to economic savings. Additionally, the use of high preheat temperatures can result in improved selectivity to olefin product. It has also be found that the use of high preheat temperatures enhances the stability of the reaction within the catalyst system thereby leading to higher sustainable superficial feed velocities, and also reduces the thermal gradient experienced across the catalyst.

The process of the present invention may suitably be carried out at a catalyst exit temperature in the range 600° C. to 1200° C., preferably, in the range 850° C. to 1050° C. and, most preferably, in the range 900° C. to 1000° C.

The process of the present invention is usually operated at a pressure of greater than 0.5 barg. Preferably the autothermal cracking process is operated at a pressure of between 0.5-40 barg and advantageously between 10-30 barg e.g. 15-25 barg.

The reaction products are preferably quenched as they emerge from the reaction chamber to avoid further reactions taking place. Usually the product stream is cooled to between 750-600° C. within less than 100 milliseconds of formation, preferably within 50 milliseconds of formation and most preferably within 20 milliseconds of formation e.g. within 10 milliseconds of formation.

Wherein the autothermal cracking process is operated at a pressure of 5-20 barg usually the products are quenched and the temperature cooled to between 750-600° C. within 20 milliseconds of formation. Advantageously wherein the autothermal cracking process is operated at a pressure of greater than 20 barg the products are quenched and the temperature cooled to between 750-600° C. within 10 milliseconds of formation.

EXAMPLES

Preparation of the Catalysts

Catalysts A to D.

Alpha alumina foams, each having an outer diameter (OD) of 10 mm, were purchased from Vesuvius High Tech and had a pore size of either 30 ppi (pores per inch) (catalysts A, B and C) or 45 ppi (catalyst D) and a density between 85 and 90% of the theoretical value.

The foams were repeatedly impregnated by immersion in a solution of tetraamineplatinum (II) chloride; said solution containing sufficient salt to achieve a nominal Pt loading of 3 wt % if all the metal in the respective salt were incorporated into the final catalyst formulation.

Between impregnations excess solution was removed from the foams, which were then dried in air at ca. 120° C. for approximately 20 minutes. After all the metal salt had been incorporated, the foams were calcined in air at 900° C. for approximately 6 hours then cooled to room temperature.

Catalyst E.

Straight channel cordierite monoliths, having an outer diameter (OD) of 10 mm, were purchased from Corning and were thin walled with 400 cells per inch (cpi). The monoliths were impregnated with platinum to achieve a nominal Pt loading of 3 wt %. The catalyst was then calcined at 900° C. for 6 hours under air and then cooled to room temperature.

Experimental Setup

The experiments were performed in an autothermal cracking reaction apparatus comprising a steel reactor in an electrically heated furnace.

Feed gases (hydrogen, nitrogen and oxygen) were supplied from cylinders via mass flow controllers into two manifolds, one for oxygen, the second for all other feeds. Light naphtha was used as the hydrocarbon feed for all experiments, and was pumped into a vaporiser along with the hydrogen and nitrogen, and the stream was pre-heated to 300° C. The oxygen was also heated to a similar temperature and the two streams were then mixed immediately before contacting the catalyst system.

The catalyst system consisted of blocks of catalyst, as listed in Table 1. The catalyst system was packed into a glass catalyst holder, along with a non-catalytic resistance zone upstream of the catalyst system. The non-catalytic resistance zone was an alpha alumina foam of 10 mm OD, 30 mm length and having 30 pores per inch (ppi). For the examples below, the furnace set to 800° C., the naphtha was fed at a constant rate of 5.0 g/min, the nitrogen was fed at a constant 0.42 nl/min (and which was used as an internal standard) and the ratio of hydrogen to oxygen was set at 0.5 (by volume).

For each catalyst system the oxygen flows were varied from 0.87 nl/min to 1.17 nl/min in nominal increments of 0.06 nl/min.

For the purposes of the examples, hydrocarbon conversion was calculated based on the $C_1$-$C_4$ and aromatics components of the stream, and was defined by the following:

feed rate*(1-mass fraction of $C_5$-$C_9$ non aromatic components in the products stream).

The product gases were sampled and analysed by both on-line gas chromatography (for $C_4$ components and above) and by off-line gas chromatography ($C_1$-$C_4$).

Results

The comparative results at 85% conversion are shown in Table 1. For all examples, 85% conversion was obtained at oxygen levels in the range 1.0 to 1.06 nl/min.

Comparative Examples A and B show the results obtained when using the same, foam, catalyst support as both the first and second catalyst support. These examples also use catalyst systems of the same nominal composition and hence show the reproducibility of the results.

Examples 1 to 3 show that the use of a foam as the first support with a cordierite monolith as the second support provides increased ethylene yield compared to the use the same foam for both the first and second catalyst supports. Examples 1 and 2 use catalyst systems of the same nominal composition and again show the reproducibility of the results.

TABLE 1

Results for autothermal cracking of naphtha at a hydrocarbon conversion of 85%.

| Experiment | Comparative Example A | Comparative Example B | 1 | 2 | 3 |
|---|---|---|---|---|---|
| First Catalyst | A | B | A | C | D |
| Bed Length | 30 mm | 30 mm | 30 mm | 30 mm | 15 mm |
| Second Catalyst | A | B | E | E | E |
| Bed Length | 30 mm | 30 mm | 30 mm | 30 mm | 30 mm |
| $O_2$ Conversion | >99% | >99% | >99% | >99% | >99% |
| Yields (g/min) | | | | | |
| $H_2$ | 0.88 | 0.81 | 1.34 | 1.28 | 1.62 |
| CO | 15.5 | 15.8 | 18.0 | 19.5 | 22.0 |

TABLE 1-continued

Results for autothermal cracking of naphtha at a hydrocarbon conversion of 85%.

| Experiment | Comparative Example A | Comparative Example B | 1 | 2 | 3 |
|---|---|---|---|---|---|
| $CO_2$ | 3.0 | 2.6 | 6.5 | 5.5 | 6.0 |
| $CH_4$ | 10.1 | 9.8 | 9.2 | 9.2 | 9.4 |
| $C_2H_4$ | 21.1 | 20.7 | 22.0 | 22.4 | 22.3 |
| $C_2H_6$ | 2.4 | 2.4 | 2.3 | 2.4 | 2.4 |

(All heavier components had the same yields within experimental error.)

The invention claimed is:

1. A process for the production of an olefin, said process comprising passing a mixture of a hydrocarbon and an oxygen-containing gas over a catalyst system capable of supporting combustion beyond the fuel rich limit of flammability, which catalyst system comprises a catalytic component, a first support and a second support, wherein the catalytic component is present on both the first and the second support, wherein the first support and second support differ in at least one of support material, support type and/or support structural dimension and wherein the first and/or second supports are in the form of ceramic foam or ceramic monolith and comprise a series of blocks or layers which are arranged such that they tessellate together to leave no gaps, the blocks or layers being tiled within a reactor in different directions in a manner such that tiles of a layer either above or below do not exactly overlap with any neighboring layer.

2. A process as claimed in claim 1, wherein hydrogen is co-fed with the hydrocarbon and oxygen-containing gas into the reactor.

3. A process as claimed in claim 1, wherein the catalytic component comprises a Group VIIIB metal.

4. A process as claimed in claim 1, wherein the first support and the second support have different structural dimensions.

5. A process as claimed in claim 1, wherein the first support is formed from the same material and has the same structural dimensions as the second support, but the supports are of different support types.

6. A process as claimed in claim 1, wherein one support is located upstream of the other with respect to the directional flow of reactants.

7. A process as claimed in claim 6, wherein the first support is located in a reactor upstream of the second support with respect to the directional flow of the reactants, and the first support provides a higher pressure drop per unit length (in the direction of flow of the reactants) than the second support.

8. A process as claimed in claim 6, wherein the first support is located in a reactor upstream of the second support with respect to the directional flow of the reactants and down the sides of the second support.

9. A process as claimed in claim 7, wherein the first support is a foam and the second support is a monolith, and the first support is located in a reactor upstream of the second support with respect to the directional flow of reactants.

10. A process as claimed in claim 7, wherein the first support is a porous foam comprising small pores and the second support is a foam comprising larger pores, and the first support is located in a reactor upstream of the second support with respect to the directional flow of reactants.

11. A process as claimed in claim 1, wherein a non catalytic resistance zone is located upstream of the catalyst system.

12. A process as claimed in claim 1, wherein the ratio of hydrocarbon to oxygen-containing gas is 5 to 16 times the stoichiometric ratio of hydrocarbon to oxygen-containing gas required for complete combustion of the hydrocarbon to carbon dioxide and water.

13. A catalyst system capable of supporting combustion beyond the fuel rich limit of flammability comprising a catalytic component, a first support and a second support, wherein the catalytic component is present on both the first support and the second support, wherein the first support and second support differ in at least one of support material, support type and/or support structural dimension and further wherein the first and/or second supports are in the form of a ceramic foam or ceramic monolith and comprise a series of blocks or layers which are arranged such that they tessellate together to leave no gaps and the blocks or layers are tiled within a reactor in different directions in a manner such that tiles of a layer either above or below do not exactly overlap with any neighboring layer.

14. A catalyst system as claimed in claim 13, wherein first support and the second support have different structural dimensions.

15. A process as claimed in claim 4, wherein the first support is formed from the same material and is of the same support type as the second support.

16. A catalyst system as claimed in claim 15, wherein the first support is formed from the same material and is of the same support type as the second support.

* * * * *